US008569209B2

(12) United States Patent
Vermeer et al.

(10) Patent No.: US 8,569,209 B2
(45) Date of Patent: Oct. 29, 2013

(54) THICKENER FOR PLANT-COMPATIBLE CONCENTRATES THAT CAN BE DISPERSED IN WATER

(75) Inventors: Ronald Vermeer, Monheim (DE); Heike Hungenberg, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 176 days.

(21) Appl. No.: 13/055,374

(22) PCT Filed: Jul. 11, 2009

(86) PCT No.: PCT/EP2009/005062
§ 371 (c)(1),
(2), (4) Date: Apr. 7, 2011

(87) PCT Pub. No.: WO2010/009822
PCT Pub. Date: Jan. 28, 2010

(65) Prior Publication Data
US 2011/0177948 A1 Jul. 21, 2011

(30) Foreign Application Priority Data

Jul. 24, 2008 (EP) ..................................... 08161062

(51) Int. Cl.
*A01N 25/26* (2006.01)
*A01N 43/40* (2006.01)
*A01N 43/48* (2006.01)
*A01N 35/00* (2006.01)
*A01N 43/36* (2006.01)

(52) U.S. Cl.
USPC .......... 504/100; 504/244; 504/252; 504/253; 504/272; 504/273; 504/283; 504/348

(58) Field of Classification Search
None
See application file for complete search history.

(56) References Cited

U.S. PATENT DOCUMENTS

| 4,443,971 | A | 4/1984 | Chaleff |
| 4,761,373 | A | 8/1988 | Anderson et al. |
| 5,013,659 | A | 5/1991 | Bedbrook et al. |
| 5,162,602 | A | 11/1992 | Somers et al. |
| 5,705,476 | A | 1/1998 | Hoffarth |
| 6,602,823 | B1 | 8/2003 | Röchling et al. |
| 6,664,213 | B1 | 12/2003 | Furusawa et al. |
| 7,473,309 | B2 | 1/2009 | Tsumuraya |
| 2002/0155954 | A1 | 10/2002 | Aven |
| 2006/0116414 | A1 | 6/2006 | Dunkel et al. |
| 2007/0293550 | A1 | 12/2007 | Rochling et al. |
| 2008/0318791 | A1 | 12/2008 | Baur et al. |
| 2009/0247597 | A1 | 10/2009 | Vermeer et al. |
| 2010/0305170 | A1 | 12/2010 | Erdelen et al. |

FOREIGN PATENT DOCUMENTS

| EP | 0 142 924 B1 | 5/1985 |
| EP | 0 193 259 B1 | 9/1986 |
| EP | 0 221 044 B1 | 5/1987 |
| EP | 0 257 993 B1 | 3/1988 |
| EP | 0 681 865 B1 | 11/1995 |
| EP | 1 905 300 A1 | 4/2008 |
| JP | 5-133904 A | 6/1993 |
| JP | 2006-257376 A | 9/2006 |
| JP | 2007-119439 A | 5/2007 |
| JP | 2006-63298 A | 3/2008 |
| WO | WO 84/02919 A1 | 8/1984 |
| WO | WO 91/13972 A1 | 9/1991 |
| WO | WO 91/19806 A1 | 12/1991 |
| WO | WO 92/11376 A1 | 7/1992 |
| WO | WO 92/14827 A1 | 9/1992 |
| WO | WO 98/35553 A1 | 8/1998 |
| WO | WO 00/35278 A1 | 6/2000 |
| WO | WO 01/13724 A1 | 3/2001 |
| WO | WO 03/070705 A1 | 8/2003 |
| WO | WO 2004/016088 | 2/2004 |

OTHER PUBLICATIONS

Braun, H., et al., "The general mitochondrial processing peptidase from potato is an integral part of cytochrome *c* reductase of the respiratory chain," *EMBO Journal 11*:.3219-3227, Oxford University Press (1992).

Christou, P., "Transformation technology," *Trends in Plant Science 1*: 423-431, Elsevier Science Ltd. (1996).

Dea, I.C.M., "Industrial polysaccharides," *Pure & Appl. Chem. 61*:1315-22, Pergamon Press, Great Britain (1989).

Diltz, S., et al., "Location of *O*-acetyl groups in S-657 using the reductive-cleavage method," *Carbohydrate Research 331*: 265-270, Elsevier Scientific Ltd., Netherlands (2001).

Haefs, R., et al., "Studies on a new group of biodegradable surfactants for glyphosate," Pest Manag. Sci. 58: 825-833, Society of Chemical Industry (2002).

International Search Report for International Application No. PCT/EP2009/005062, European Patent Office, Netherlands, mailed on Dec. 11, 2009.

Sonnewald, U., et al., "Transgenic tobacco plants expressing yeast-derived invertase in either the cytosol, vacuole or apoplast: a powerful tool for studying sucrose metabolism and sink/source interactions," *The Plant Journal* 1:95-106, John Wiley & Sons, Inc. (1991).

(Continued)

*Primary Examiner* — Alton Pryor
(74) *Attorney, Agent, or Firm* — Sterne, Kessler, Goldstein & Fox P.L.L.C.

(57) ABSTRACT

The present invention relates to novel water-dispersed agrochemical formulations, for example water-based suspension concentrates, of active agrochemical ingredients, comprising a penetrant and a thickener from the class of the anionic polysaccharides which contains, as the repetitive base unit in the main chain, four sugar molecules (glucose, glucuronic acid, glucose, rhamnose), to a process for producing these formulations and to the use thereof for application of the active ingredients present.

5 Claims, No Drawings

(56) References Cited

OTHER PUBLICATIONS

Wolter, F.P., et al.,"*rbcS* Genes in *Solanum tuberosum*: Conservation of Transit Peptide and Exon Shuffling During Evolution," Proc. Natl. Acad. Sci. USA 85: 846-850, United States National Academy of Sciences (1988).

Database WPI Week 199327, XP 002511829, Abstract for JP 05139904, published Jun. 8, 1993.

Office Action mailed Oct. 11, 2011, in U.S. Appl. No. 12/814,869, inventors Erdelen, C., et al., filed Jun. 14, 2010, U.S. Patent and Trademark Office, Alexandria, VA.

Office Action mailed May 10, 2012, in U.S. Appl. No. 12/814,869, inventors Erdelen, C., et al., filed Jun. 14, 2010, U.S. Patent and Trademark Office, Alexandria, VA.

Unverified partial English translation of Japanese Patent Application No. JP 5-139904 A, published Jun. 8, 1993 (13 pages), with English abstract, European Patent Office, Espacenet database (2012).

Unverified partial English translation of Japanese Patent Application No. JP 2006-63298 A, published Mar. 9, 2006 (1 page), with English abstract, European Patent Office, Espacenet database (2012).

Unverified partial English translation of Japanese Patent Application No. JP 2006-257376 A, published Sep. 28, 2006 (1 page), with English abstract, European Patent Office, Espacenet database (2012).

Unverified partial English translation of Japanese Patent Application No. JP 2007-119439 A, published May 17, 2007 (2 pages), with English abstract, European Patent Office, Espacenet database (2012).

THICKENER FOR PLANT-COMPATIBLE CONCENTRATES THAT CAN BE DISPERSED IN WATER

The present invention relates to novel water-dispersible agrochemical formulations, for example water-based suspension concentrates, of active agrochemical ingredients, to a process for producing these formulations and to the use thereof for application of the active ingredients present.

To display biological efficacy, systemic active agrochemical ingredients, especially systemic insecticides and fungicides, need a formulation which enables uptake of the active ingredients into the plant/the target organisms. Typically, systemic active agrochemical ingredients are therefore formulated as an emulsion concentrate (EC), soluble liquid (SL) and/or oil-based suspension concentrate (OD). In an EC and SL formulation the active ingredient is in dissolved form, and in an OD formulation in solid form. A suspension concentrate (SC) too is generally technically possible. The description which follows is of suspension concentrates only, though this also refers to other formulation types in which the active ingredient is in a water-dispersed form. In the case of use of SC formulations, however, to achieve sufficient biological efficacy, it is necessary that the active ingredient is combined with an additive. An additive in this context is a component which improves the biological efficacy of the active ingredient without itself exhibiting biological efficacy. More particularly, an additive enables/promotes the uptake of the active ingredient into the leaf (penetrant). A penetrant can be incorporated into the formulation of the active agrochemical ingredient (in-can formulation) or added to the spray liquor after dilution of the concentrated formulation (tankmix). To prevent dosage errors and to improve user safety in the application of agrochemical products, it is advantageous to incorporate the penetrants into the formulation. In addition, this avoids the unnecessary use of extra packaging material for the tankmix products.

The disadvantage of the abovementioned formulations containing penetrants is that, particularly in the case of application to leaves, fruits or other plant parts in sensitive crop plants, for example pomaceous fruit (e.g. *Malus domestica, Pyrus communis*), stone fruit (*Prunus armeniaca, Prunus domestica, Prunus persica*), citrus crops, vegetables, for example bell pepper (*Capsicum annuum*), and cantaloupe (*Cucumis melo*), and also ornamental plants such as roses, after application and drying of the spray liquid, the spray liquor residue can lead to plant damage.

There are already some known water-based suspension concentrates of active agrochemical ingredients, which comprise penetrants and exhibit low levels of plant damage. For instance, Pest. Manag. Sci. 58, 825-833 (2002) describes triglyceride ethoxylates (Agnique®RSO Series), which are recommended as tankmix penetrants for systemic water-soluble active agrochemical ingredients. A stated advantage of these assistants is plant compatibility on weeds. This is characterized by a lack of influence on photosynthesis, which is advantageous for the systemic action of phloem-mobile active ingredients such as glyphosate. However, the spray liquor concentrations needed for sufficient uptake of active ingredient were between 1 and 10 g/l, which cannot be reconciled with an "in-can" formulation.

U.S. 2002/0155954 specifies triglyceride ethoxylates which lower the surface tension of the spray liquor below 40 mN/m as an additive. This application describes the triglyceride ethoxylates in an "in-can" formulation. The formulations described in this document contain xanthan gum as a thickener (commercially available, for example, as Kelzan S® from CP Kelco).

EP-A 1905300 describes triglyceride ethoxylate-containing suspension concentrates. A disadvantage of these formulations is that the addition of large proportions of the polyalkoxyalkylene triglycerides to the aqueous formulation increases the viscosity of the formulation. In the case of surfactant concentrations significantly above the critical micelle concentration, the surfactant molecules congregate in higher structures, which leads to a higher viscosity. In addition to these surfactant molecules, a particular amount of a thicker (xanthan gum is generally used for this purpose) is also added to the suspension concentrates. This thickener is needed to prevent the sedimentation of the active ingredient particles after prolonged storage. A high viscosity—caused by a supramolecular surfactant structure—is not sufficient to prevent the sedimentation process. A problem with this procedure is that it is often possible to add only too small an amount of thickener, because excessively high viscosities are otherwise obtained. Too small an amount of thickener leads to the effect that the suspension concentrates exhibit phase separation in the bottle within a very short time, which can lead to incorrect dosages on the part of the user. Excessively high viscosities of the suspension concentrates are problematic for the user, because they cause the formulations to have poor flow out of the bottle.

It is therefore an object of the present invention to provide stable, storable, water-based suspension concentrates which comprise penetrants, without occurrence of significant phase separation after storage.

It has been found that this problem is solved by water-dispersible agrochemical formulations comprising a penetrant, especially from the class of the polyalkoxytriglycerides, and a thickener from the class of the anionic polysaccharides which contains, as the repetitive base unit in the main chain, four sugar molecules (glucose, glucuronic acid, glucose, rhamnose). The thickeners described here are known from the mineral oil industry and concrete industry, but unknown in crop protection formulations.

The present invention thus provides liquid suspension concentrates comprising
- at least one active agrochemical ingredient solid at room temperature and
- at least one penetrant and
- at least one thickener from the class of the anionic polysaccharides which contains, as the repetitive base unit in the main chain, four sugar molecules (glucose, glucuronic acid, glucose, rhamnose).

The inventive compositions are preferably liquid suspension concentrates comprising
- at least one active agrochemical ingredient solid at room temperature and
- at least one penetrant from the class of the polyalkoxytriglycerides
- at least one thickener from the class of the anionic polysaccharides which contains, as the repetitive base unit in the main chain, four sugar molecules (glucose, glucuronic acid, glucose, rhamnose).

The inventive compositions are more preferably liquid suspension concentrates comprising
- at least one active agrochemical ingredient solid at room temperature,
- at least one penetrant from the class of the polyalkoxytriglycerides, the triglyceride being of plant origin, at least one thickener from the class of the anionic polysaccharides which contains, as the repetitive base unit in the main chain, four sugar molecules (glucose, glucuronic acid, glucose, rhamnose).

In addition, it has been found that inventive water-based suspension concentrates can be prepared by mixing at least one active agrochemical ingredient solid at room temperature,
at least one penetrant and
at least one thickener from the class of the anionic polysaccharides which contains, as the repetitive base unit in the main chain, four sugar molecules (glucose, glucuronic acid, glucose, rhamnose)
with one another, and then optionally grinding the resulting suspension.

In addition, it has been found that inventive suspension concentrates, preferably based on water, can be prepared by mixing at least one active agrochemical ingredient solid at room temperature,
at least one penetrant from the class of the polyalkoxytriglycerides,
at least one thickener from the class of the anionic polysaccharides which contains, as the repetitive base unit in the main chain, four sugar molecules (glucose, glucuronic acid, glucose, rhamnose)
with one another, and then optionally grinding the resulting suspension.

Finally, it has been found that the inventive suspension concentrates are very suitable for application of the active agrochemical ingredients present to plants and/or the habitat thereof.

It is surprising that it is possible with the inventive compositions to develop formulations which have a sufficient viscosity, even though they contain only a small amount of thickener.

Moreover, it is extremely surprising that the inventive suspension concentrates have a very good stability, even after storage at elevated temperatures. The low thickener concentrations employed would be expected to lead to phase separation.

In addition, it has been found that, surprisingly, the inventive compositions have better biological efficacy than the formulations based on xanthan gum which are already known. It was not foreseeable for the person skilled in the art that the uptake of the active ingredient can be influenced by the thickener.

Finally, it is considered to be surprising that, even though the inventive compositions lead to a higher uptake, plant compatibility is not worsened by the inventive compositions.

Preferred embodiments of the subject matter of the invention are described hereinafter.

Useful penetrants in the present context are polyalkoxytriglycerides. Polyalkoxytriglycerides can be prepared by alkoxylating triglycerides. The alkoxylation of triglycerides leads to substance mixtures wherein 1 to 3 of the side chains are alkoxylated. Alkoxylation can be divided into ethoxylation, propoxylation, butoxylation, or a mixture of these operations. The length of each of the unmodified side chains may vary, independently of the other side chains in the same molecule, between 9 and 24, preferably between 12 and 22 and very preferably between 14 and 20 carbon atoms. These aliphatic side chains may be straight or branched.

In a preferred embodiment of the present invention, the polyalkoxytriglycerides are obtained by ethoxylation of triglycerides.

In a particularly preferred embodiment of the present invention, the polyalkoxytriglycerides are obtained by ethoxylation of castor oil, rapeseed oil, corn oil, palm kernel oil or almond oil.

In a further particularly preferred embodiment of the present invention, the polyalkoxytriglycerides are obtained by ethoxylation of castor oil or rapeseed oil.

In a very particularly preferred embodiment of the present invention, the polyalkoxytriglycerides are obtained by ethoxylation of castor oil or rapeseed oil, the degree of ethoxylation being between 30% by weight and 80% by weight.

In an especially preferred embodiment of the present invention, the polyalkoxytriglycerides are obtained by ethoxylation of rapeseed oil, the degree of ethoxylation being between 50% by weight and 80% by weight.

In a further especially preferred embodiment of the present invention, the polyalkoxytriglycerides are obtained by ethoxylation of castor oil, the degree of ethoxylation being between 30% by weight and 50% by weight.

Corresponding polyalkoxytriglycerides are known or can be prepared by known methods (they are available commercially, for example, as Crovol® A 70 UK, Crovol® CR 70 G, Crovol® M 70 or Crovol® PK 70 from Croda, or Berol® 904 from AKZO Nobel).

Useful penetrants in the present context are likewise all those substances which are typically used to improve the penetration of active agrochemical ingredients into plants.

Preferred penetrants are alkanol alkoxylates of the formula $$R\text{—}O\text{-}(\text{-}AO)_m R' \qquad (I)$$

in which
R is straight-chain or branched alkyl having 4 to 20 carbon atoms,
R' is H, methyl, ethyl, n-propyl, i-propyl, n-butyl, i-butyl, t-butyl, n-pentyl or n-hexyl,
AO is an ethylene oxide radical, a propylene oxide radical, a butylene oxide radical or mixtures of ethylene oxide and propylene oxide radicals or butylene oxide radicals, and
m is from 2 to 30.

A particularly preferred group of penetrants is that of alkanol alkoxylates of the formula $$R\text{—}O\text{-}(\text{-}EO\text{—})_n\text{—}R' \qquad (I\text{-}a)$$

in which
R is as defined above,
R' is as defined above,
EO is —CH$_2$—CH$_2$—O— and
n is from 2 to 20.

A further particularly preferred group of penetrants is that of alkanol alkoxylates of the formula $$R\text{—}O\text{-}(\text{-}EO\text{—})_p\text{—}(\text{—}PO\text{—})_q\text{—}R' \qquad (I\text{-}b)$$

or $$R\text{—}O\text{—}(\text{—}PO\text{-})_r\text{-}(EO\text{—})_s\text{—}R' \qquad (I\text{-}c)$$

in which
EO, R and R' are each as defined above,
PO is

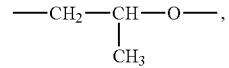

p is from 1 to 10 and
q is from 1 to 10.

A further particularly preferred group of penetrants is that of alkanol alkoxylates of the formula $$R\text{—}O\text{-}(\text{-}EO\text{—})_p\text{—}(\text{—}BO\text{—})_q\text{—}R' \quad (I\text{-}d)$$

or $$R\text{—}O\text{—}(\text{—}BO\text{-})_r\text{-}(\text{-}EO\text{—})_s\text{—}R' \quad (I\text{-}e)$$

in which
EO, R und R' are each as defined above,
BO is $$\text{—}CH_2\text{—}CH_2\text{—}\underset{\underset{CH_3}{|}}{CH}\text{—}O\text{—},$$

p is from 1 to 10 and
q is from 1 to 10.

A further particularly preferred group of penetrants is that of alkanol alkoxylates of the formula $$CH_3\text{—}(CH_2)_t\text{—}CH_2\text{—}O\text{—}(\text{—}CH_2\text{—}CH_2\text{—}O\text{—})_u\text{—}R' \quad (I\text{-}f)$$

in which
R' is as defined above,
t is from 8 to 13,
u is from 6 to 17.

In the formulae specified above,
R is preferably butyl, i-butyl, n-pentyl, i-pentyl, neopentyl, n-hexyl, i-hexyl, n-octyl, i-octyl, 2-ethylhexyl, nonyl, i-nonyl, decyl, n-dodecyl, i-dodecyl, lauryl, myristyl, i-tridecyl, trimethylnonyl, palmityl, stearyl or eicosyl.

One example of an alkanol alkoxylate of the formula (I-d) is the compound of the formula $$CH_3\text{—}(CH_2)_{10}\text{—}O\text{-}(\text{-}EO\text{—})_6\text{—}(\text{—}BO\text{—})_2\text{—}CH_3 \quad (I\text{-}d\text{-}1)$$

in which EO and BO are each as defined above, and the numbers 10, 6 and 2 are average values.

The alkanol alkoxylates are defined in general terms by the above formulae. These substances are mixtures of substances of the stated type with different chain lengths. The indices are therefore averages which may also deviate from whole numbers.

The alkanol alkoxylates of the formulae specified are known or can be prepared by known methods (cf. WO 98-35 553, WO 00-35 278 und EP-A 0 681 865).

The thickeners used in the present context are anionic polysaccharides which contain, as the repetitive base unit in the main chain, four sugar molecules (glucose, glucuronic acid, glucose, rhamnose). As a side chain, these polysaccharides may contain one rhamnose unit, one mannose unit or two rhamnose units. Polysaccharides with one rhamnose or one mannose side chain are known by the name welan gum (trade name, for example, Kelco crete K1C376). Those with one side chain which contains two rhamnose molecules are known as diutan gum. These polysaccharides can be obtained biosynthetically or biotechnologically, by means of certain microorganisms. Examples include the polysaccharides which are separated out after fermentation by the *Sphingomonas* bacterial strain.

Preference is given to using diutan gum as the thickener. The structure of diutan gum is described in the literature (Diltz et al., "Location of O-acetyl Groups in S-657 Using the Reductive-Cleavage Method," CARBOHYDRATE RESEARCH, Vol. 331, p. 265-270 (2001)). Corresponding polysaccharides are known or can be prepared by known methods (cf. Kelco Vis-DG (oil industry) or Kelco Crete 200 (concrete industry) from CP Kelco).

The active ingredients used in the inventive formulations may be any active agrochemical ingredients solid at room temperature.

Preference is given to systemic fungicides, insecticides and herbicides.

Particular preference is given to active ingredients from the classes of the azole fungicides (azaconazole, bitertanol, bromuconazole, cyproconazole, diclobutrazole, difenoconazole, diniconazole, diniconazole-M, epoxiconazole, etaconazole, fenarimol, fenbuconazole, fluquinconazole, flurprimidol, flusilazole, flutriafol, furconazole, furconazole-cis, hexaconazole, imazalil, imazalil sulfate, imibenconazole, ipconazole, metconazole, myclobutanil, nuarimol, oxpoconazole, paclobutrazole, penconazole, pefurazoate, prochloraz, propiconazole, prothioconazole, pyrifenox, simeconazole, tebuconazole, tetraconazole, triadimefon, triadimenol, triflumizole, triforin, triticonazole, uniconazole, voriconazole, viniconazole), strobilurin fungicides (azoxystrobin, dimoxystrobin, fluoxastrobin, kresoxim-methyl, metominostrobin, orysastrobin, picoxystrobin, pyraclostrobin, trifloxystrobin), fungicidal inhibitors of complex II of the respiratory chain (e.g. bixafen, boscalid, carboxin, fenfuram, fluopyram, flutolanil, furametpyr, furmecyclox, isopyrazam, mepronil, oxycarboxin, penthiopyrad, sedaxane, thifluzamide), chloronicotinyl insecticides (clothianidin, dinotefuran, imidacloprid, thiamethoxam, nitenpyram, nithiazine, acetamiprid, imidacloprid, nitenpyram, thiacloprid), the insecticidal ketoenols (spirodiclofen, spiromesifen, spirotetramate), fiproles (fiprole, ethiprole) and butenolides, and also pymetrozines, fluopicolide. Likewise particularly preferred are herbicides, especially sulfonylureas, triketones and herbicidal ketoenols, and also safeners.

Very particularly preferred active ingredients are
The Fungicides
tebuconazole,
prothioconazole,
bixafen (known from WO 03/070705),
fluopyram (known from WO 04/16088),
trifloxystrobin,
fluoxastrobin,
pyraclostrobin,
azoxystrobin,
fluopicolide
The Insecticides
imidacloprid,
thiamethoxam,
clothianidin,
thiacloprid,
spirotetramat,
fipronil,
ethiprol and
The Herbicides
thiencarbazone
sulcotrione,
mesotrione,
tembotrione,
pyrasulfotole,
iodosulfuron,
mesosulfuron and
foramsulfuron.

Especially preferred active ingredients are spirotetramat, tebuconazole, prothioconazole, tembotrione, thiacloprid, fluopicolide and imidacloprid.

The formulations may optionally comprise one or more additives from the groups of the nonionic surfactants and/or anionic surfactants, the frost protectants, the foam inhibitors, the preservatives, the antioxidants, the spreaders and/or the dyes.

Useful nonionic surfactants include all substances of this type which are typically usable in agrochemical compositions. Preference is given to polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, copolymers of polyvinylacetate and polyvinylpyrrolidone, and copolymers of (meth)acrylic acid and (meth)acrylic esters, and additionally alkyl ethoxylates and alkylaryl ethoxylates, which may optionally be phosphated and optionally be neutralized with bases, polyoxyamine derivatives and nonylphenol ethoxylates.

Useful anionic surfactants include all substances of this type which are typically usable in agrochemical compositions. Preference is given to alkali metal salts and alkaline earth metal salts of alkylsulfonic acids or alkylarylsulfonic acids.

A further preferred group of anionic surfactants and/or dispersing assistants is that of salts of polystyrenesulfonic acids, salts of polyvinylsulfonic acids, salts of naphthalenesulfonic acid-formaldehyde condensation products, salts of condensation products of naphthalenesulfonic acid, phenolsulfonic acid and formaldehyde, and salts of lignosulfonic acid.

Useful frost protectants include all substances of this type which are typically usable in agrochemical compositions. Preference is given to urea, glycerol or propylene glycol. A further preferred group of frost protectants is that of additives from the group of the polyglycerols or polyglycerol derivatives.

Useful foam inhibitors are all substances typically usable for this purpose in agrochemical compositions. Preference is given to silicone oils and magnesium stearate.

Useful preservatives include all substances which are typically usable for this purpose in agrochemical compositions of this type. Examples includes Preventol® (from Lanxess AG) and Proxel®.

Useful antioxidants are all substances typically usable for this purpose in agrochemical compositions. Preference is given to butylhydroxytoluene (2,6-di-t-butyl-4-methylphenol, BHT).

Useful spreaders are all substances typically usable for this purpose in agrochemical compositions. Preference is given to polyether- or organomodified polysiloxanes.

Useful dyes are all substances typically usable for this purpose in agrochemical compositions. Examples include titanium dioxide, pigment black, zinc oxide and blue pigments, and also Permanent Red FGR.

The inventive compositions comprise
generally between 1 and 60% by weight of one or more of the active agrochemical ingredients usable in accordance with the invention, preferably 5 to 50% by weight and more preferably 10 to 30% by weight,
generally between 1 and 50% by weight of at least one penetrant, preferably 2 to 30% by weight and more preferably 5 to 20% by weight,
generally between 0.005 and 1% by weight of at least one thickener from the group of the anionic polysaccharides which contains, as the repetitive base unit in the main chain, four sugar molecules (glucose, glucuronic acid, glucose, rhamnose).

The formulations may optionally comprise one or more additives from the groups of the nonionic surfactants and/or anionic surfactants, the frost protectants, the foam inhibitors, the preservatives, the antioxidants, the spreaders and/or the dyes.

The inventive suspension concentrates are produced by mixing the components with one another in the particular ratios desired. The sequence in which the constituents are combined with one another may be as desired. It is appropriate to use the solid components in the finely ground state. However, it is also possible to subject the suspension formed after the combination of the constituents first to a coarse and then to a fine grinding step, such that the mean particle size is below 20 μm. Preference is given to suspension concentrates in which the solid particles have a mean particle size between 1 and 10 μm.

In the course of performance of the process according to the invention, the temperatures can be varied within a particular range. In general, working temperatures are between 10° C. and 60° C., preferably between 15° C. and 40° C.

Useful equipment for performance of the process according to the invention is customary mixing and grinding equipment which is used to prepare agrochemical formulations.

The inventive compositions are formulations which remain stable even after prolonged storage at elevated temperatures or under cold conditions, since no crystal growth is observed. They can be converted to homogeneous spray liquids by diluting with water.

The application rate of the inventive compositions can be varied within a relatively wide range. It is guided by the active agrochemical ingredients in question and by the content thereof in the compositions.

The inventive compositions comprising at least one of the inventive active insecticidal ingredients, in combination with good plant tolerance, favorable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp.,

*Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnostema consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Stemechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is furthermore possible to control Protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pin, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare, Oniscus asellus* and *Porcellio scaber*.

From the order of the Isoptera, for example, *Reticulitermes* spp. and *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythinma separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp. and *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni* and *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans* and *Xiphinema* spp.

In some cases, the inventive compositions can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (Mycoplasma-like organisms) and RLO (Rickettsia-like organisms).

In addition to the active agrochemical ingredients already mentioned above, further co-components present in the inventive compositions may be further active ingredients such as insecticides, attractants, sterilants, bactericides, acaricides, nematicides, fungicides, growth regulators, herbicides, safeners, fertilizers or semiochemicals.

Particularly favorable examples of co-components are the following compounds:

Fungicides:

Inhibitors of nucleic acid synthesis: benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid Inhibitors of mitosis and cell division: benomyl, carbendazim, diethofencarb, ethaboxam, fuberidazole, pencycuron, thiabendazole, thiophanat-methyl, zoxamide Inhibitors of respiratory chain complex I: diflumetorim Inhibitors of respiratory chain complex II: boscalid, carboxin, fenfuram, flutolanil, furametpyr, furmecyclox, mepronil, oxycarboxin, penthiopyrad, thifluzamide Decouplers: dinocap, fluazinam Inhibitors of ATP production: fentin acetate, fentin chloride, fentin hydroxide, silthiofam Inhibitors of amino acid biosynthesis and protein biosynthesis: andoprim, blasticidin-S, cyprodinil, kasugamycin, kasugamycin hydrochloride hydrate, mepanipyrim, pyrimethanil Inhibitors of signal transduction: fenpiclonil, fludioxonil, quinoxyfen Inhibitors of lipid and membrane synthesis: chlozolinate, iprodione, procymidone, vinclozolin, ampropylfos, potassium-ampropylfos, edifenphos, etridiazole, iprobenfos (IBP), isoprothiolane, pyrazophos, tolclofos-methyl, biphenyl, iodocarb, propamocarb, propamocarb hydrochloride, propamocarb-fosetylate Inhibitors of ergosterol biosynthesis: fenhexamid, aldimorph, dodemorph, dodemorph acetate, fenpropidin, fenpropimorph, spiroxamine, tridemorph, naftifine, pyributicarb, terbinafine Inhibitors of cell wall synthesis: benthiavalicarb, bialaphos, dimethomorph, flumorph, iprovalicarb, mandipropamid, polyoxins, polyoxorim, validamycin A Inhibitors of melanin biosynthesis: carpropamid, diclocymet, fenoxanil, phthalide, pyroquilon, tricyclazole Resistance induction: acibenzolar-S-methyl, probenazole, tiadinil Multisite: captafol, captan, chlorothalonil, copper salts such as: copper hydroxide, copper naphthenate, copper oxychloride, copper sulfate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations containing calcium polysulfide, thiram, tolylfluanid, zineb, ziram Further fungicides: amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ferimzon, flumetover, flusulfamide, fluoroimide, fosetyl-aluminum, fosetyl-calcium, fosetyl-sodium, hexachlorobenzene, 8-hydroxyquinolinsulfate, irumamycin, methasulfocarb, metrafenon, methyl isothiocyanate, mildiomycin, natamycin, nickel dimethyldithiocarbamate, nitrothal-isopropyl, octhilinon, oxamocarb, oxyfenthiin, pentachlorophenol and salts, 2-phenylphenol and salts, piperalin, propanosinsodium, proquinazid, pyribencarb, pyrrolnitrin, quintozen, tecloftalam, tecnazen, triazoxide, trichlamide, valiphenal, zarilamid, 2-(2-{[6-(3-chloro-2-methylphenoxy)-5-fluoropyrimidin-4-yl]oxy}phenyl)-2-(methoxyimino)-N-methylacetamide, 2-[[[[1-[3(1-fluoro-2-phenylethy)oxy]phenyl]ethylidene]amino]oxy]methyl-alpha-(methoxyimino)-N-methyl-alphaE-benzacetamide, cis-1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylic acid, 2,3,5,6-tetrachloro-4-(methylsulfonyl)pyridine, 2-butoxy-6-iodo-3-propylbenzopyranon-4-one, 2-chloro-N-(2,3-dihydro-1,1,3-trimethyl-1H-inden-4-yl)-3-pyridinecarboxamide, 3,4,5-trichloro-2,6-pyridinedicarbonitrile, 3,4-dichloro-N-(2-cyanophenyl) isothiazol-5-carboxamide (isotianil), 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo[1,5-a]pyrimidine-7-amine, 5-chloro-7-(4-methylpiperidin-1-yl)-6-(2,4,6-trifluorophenyl)[1,2,4]triazolo[1,5-a]pyrimidine, 5-chloro-N-[(1R)-1,2-dimethylpropyl]-6-(2,4,6-trifluorophenyl)[1,2,4]triazolo[1,5-a]pyrimidine-7-amine, methyl 2-[[[cyclopropyl[(4-methoxyphenyl)imino]methyl]thio] methyl]-alpha.-(methoxymethylene)-benzacetate, methyl 1-(2,3-dihydro-2,2-dimethyl-1H-inden-1-yl)-1H-imidazole-5-carboxylate, N-(3-ethyl-3,5,5-trimethylcyclohexyl)-3-formylamino-2-hydroxybenzamide, N-(4-chloro-2-nitrophe-nyl)-N-ethyl-4-methylbenzenesulfonamide, N-(4-chlorobenzyl)-3-[3-methoxy-4-(prop-2-yn-1-yl-oxy)phenyl]propanamide, N-[(4-chlorophenyl)(cyano)methyl]-3-[3-methoxy-4-(prop-2-yn-1-yl-oxy)phenyl]propanamide, N-(5-bromo-3-chloropyridin-2-yl)methyl-2,4-dichloronicotinamide, N-[1-(5-bromo-3-chloropyridin-2-yl)ethyl]-2,4-dichloronicotinamide, (2S)—N-[2-[4-[[3-(4-chlorophenyl)-2-propynyl]oxy]-3-methoxyphenyl]ethyl]-3-methyl-2-[(methylsulfonyl)amino]-butanamide, N-{(Z)-[(cyclopropylmethoxy)imino][6-(difluoromethoxy)-2,3- difluorophenyl]methyl}-2-benzacetamide, N-{2-[1,1'-bi(cyclopropyl)-2-yl]phenyl}-3-(difluoromethyl)-1-methyl-1H-pyrazole-4-carboxamide, N-ethyl-N-methyl-N'-{2-methyl-5-(trifluoromethyl)-4-[3-(trimethylsilyl)propoxy]phenyl}imidoformamide, O-[1-[(4-methoxyphenoxy)methyl]-2,2-dimethylpropyl]-1H-imidazole-1-carbothioic acid, 2-amino-4-methyl-N-phenyl-5-thiazolecarboxamide, 2,4-dihydro-5-methoxy-2-methyl-4-[[[[1-[3-(trifluoromethyl)phenyl]ethylidene]amino]oxy]methyl]phenyl-3H-1,2,4-triazol-3-one (CAS No. 185336-79-2), N-(6-methoxy-3-pyridinyl)cyclopropanecarboxamide.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides/Acaricides/Nematicides:

Acetylcholine Esterase (AChE) Inhibitors carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate organophosphates, for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulfone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers pyrethroids, for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmetbrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)

DDT oxadiazines, for example indoxacarb semicarbazones, for example metaflumizone (BAS3201)

acetylcholine receptor agonists/antagonists nicotine, bensultap, cartap acetylcholine receptor modulators spinosyns, for example spinosad, spinetoram GABA-controlled chloride channel antagonists organochlorines, for example camphechlor, chlordane, endosulfan, gamma-HCH, HCH, heptachlor, lindane, methoxychlor fiproles, for example acetoprole, pyrafluprole, pyriprole, vaniliprole chloride channel activators mectins, for example abamectin, emamectin, emamectin benzoate, ivermectin, lepimectin, milbemycin juvenile hormone mimetics, for example diofenolan, epofenonane, fenoxycarb, hydroprene, kinoprene, methoprene, pyriproxifen, triprene ecdysone agonists/disruptors diacylhydrazines, for example chromafenozide, halofenozide, methoxyfenozide, tebufenozide chitin biosynthesis inhibitors benzoylureas, for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron buprofezin cyromazine oxidative phosphorylation inhibitors, ATP disruptors diafenthiuron site-II electron transport inhibitors rotenone site-III electron transport inhibitors acequinocyl, fluacrypyrim microbial disruptors of the insect gut membrane bacillus thuringiensis strains lipid synthesis inhibitors tetramic acids, for example cis-3-(2,5-dimethylphenyl)-4-hydroxy-8-methoxy-1-azaspiro[4.5]dec-3-en-2-one carboxamides, for example flonicamide octopaminergic agonists, for example amitraz inhibitors of magnesium-stimulated ATPase propargite nereistoxin analogs, for example thiocyclam hydrogen oxalate, thiosultap-sodium ryanodin receptor agonists benzoic dicarboxamides, for example flubendiamide anthranilamides, for example rynaxypyr (3-bromo-N-{4-chloro-2-methyl-6-[(methylamino)-carbonyl]phenyl}-1-(3-chloropyridin-2-yl)-1H-pyrazole-5-carboxamide)

biologicals, hormones or pheromones azadirachtin, *Bacillus* spec., *Beauveria* spec., *codlemone, Metarrhizium* spec., *Paecilomyces* spec., *thuringiensin, Verticillium* spec.

active ingredients with unknown or unspecific mechanisms of action fumigants, for example aluminum phosphide, methyl bromide, sulfuryl fluoride antifeedants, for example cryolite, flonicamide, pymetrozine mite growth inhibitors, for example clofentezine, etoxazole, hexythiazox amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active ingredients, such as fertilizers, growth regulators, semiochemicals, or else with compositions for improving the plant properties, is also possible.

Inventive compositions may also, in addition to at least one compound of the formula (I), comprise at least one further active herbicidal ingredient, preferably from the group consisting of acetochlor, acifluorfen (-sodium), aclonifen, alachlor, alloxydim (-sodium), ametryne, amicarbazone, amidochlor, amidosulfuron, aminopyralid, anilofos, asulam, atrazine, azafenidin, azimsulfuron, beflubutamid, benazolin (-ethyl), benzcarbazone, benfuresate, bensulfuron (-methyl), bentazon, benzfendizone, benzobicyclon, benzofenap, benzoylprop (-ethyl), bialaphos, bifenox, bispyribac (-sodium), bromobutide, bromo:fenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flucetosulfuron, flufenacet, flufenpyr, flumetsulam, flumiclorac (-pentyl), flumioxazin, flumipropyn, flumetsulam, flumeturon, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, glufosinate (-ammonium), glyphosate (-isopropylammonium), halosafen, haloxyfop (-ethoxyethyl, -P-methyl), hexazinone, HOK-201, imazamethabenz (-methyl), imazamethapyr, imazamox, imazapic, imazapyr, imazaquin, imazethapyr, imazosulfuron, ioxynil, isopropalin, isoproturon, isouron, isoxaben, isoxachlortole, isoxaflutole, isoxapyrifop, KIH 485, lactofen, lenacil, linuron, MCPA, mecoprop, mefenacet, metamifop, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, orthosulfamuron, oryzalin, oxadiargyl, oxadiazon, oxasulfuron, oxaziclomefone, oxyfluorfen, paraquat, pelargonic acid, pendimethalin, pendralin, penoxsularn, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), pyrimisulfan, quinchlorac, quinmerac, quinoclamine, quizalofop (-P-ethyl, -P-tefuryl), rimsulfuron, sethoxydim, simazine, simetryn, sulfentrazone, sulfometuron (-methyl), sulfosate, sulfosulfuron, tebutam, tebuthiuron, tepraloxydim, terbuthylazine, terbutryn, TH-547, thenylchlor, thiafluamide, thiazopyr, thidiazimin, thifensulfuron (-methyl), thiobencarb, thiocarbazil, topramezone, tralkoxydim, triallate, triasulfuron, tribenuron (-methyl), triclopyr, tridiphane, trifluralin, trifloxysulfuron, triflusulfuron (-methyl), tritosulfuron and triflosulam.

When used in their commercial formulations and in the use forms prepared from these formulations, the inventive compositions may also be present in a mixture with synergists. Synergists are compounds by which the action of the active ingredients present in the inventive compositions is enhanced, without any need for the added synergist to itself be active.

When used in their commercial formulations and in the use forms prepared from these formulations, the inventive compositions may also be present in mixtures with inhibitors which reduce degradation of the active agrochemical ingredient present after application in the environment of the plant, on the surface of parts of plants or in plant tissues.

The active ingredient content of the use forms prepared from the commercially available formulations may vary within wide limits. The active ingredient concentration of the application forms may be from 0.00000001 to 95% by weight of active ingredient, preferably between 0.00001 and 1% by weight.

The compounds are applied in a customary manner appropriate for the use forms.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example cuttings, tubers, rhizomes, slips and seeds.

The inventive treatment of the plants and plant parts with the compositions is effected directly or by allowing them to act on the surroundings, habitat or storage space by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts" and "parts of plants" or "plant parts" have been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus possible are, for example, reduced application rates and/or a widening of the activity spectrum and/or an increase of the activity of the compounds and compositions usable according to the invention, better plant growth, increased tolerance to high or low temperatures, increased tolerance to drought or to water or soil salt content, increased flowering, easier harvesting, accelerated maturation, higher harvest yields, higher quality and/or higher nutrient value of the harvested products, increased storability and/or processability of the harvested products, which exceed the effects normally to be expected.

The transgenic plants or plant cultivars (i.e. those obtained by genetic engineering) which are to be treated with preference in accordance with the invention include all plants which, through the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active ingredients. Examples of transgenic plants which may be mentioned are the important crop plants, such as cereals (wheat, rice), maize, soya beans, potatoes, sugar beet, tomatoes, peas and other types of vegetables, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow refereed to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active ingredients, for example imidazolinones, sulfonylureas, glyphosate or phosphinotricin (for example the "PAT" gene). The genes which impart the desired traits in question may also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya bean), Knock-Out® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) also include the varieties sold under the Clearfield® name (for example maize). Of course, these statements also apply to plant cultivars which have these genetic traits or genetic traits still to be developed and will be developed and/or marketed in the future.

The plants listed can be treated particularly advantageously in accordance with the invention with the inventive compositions. The preferred ranges stated above for the compositions also apply to the treatment of these plants. Particular emphasis is given to the treatment of plants with the compositions specifically mentioned in the present text.

The inventive compositions act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella gennanica* and *Supella* spp.

From the subclass of the Acari (Acarina) and the orders of the Meta- and Mesostigmata, for example, *Argas* spp., *Omithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The inventive compositions are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. The control of these arthropods should reduce cases of death and reduced productivity (of meat, milk, wool, hides, eggs, honey etc.), such that more economic and easier animal husbandry is possible by use of the inventive compositions.

The inventive compositions are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active ingredient, such as collars, ear marks, tail marks, limb bands, halters, marking devices and the like.

When used for cattle, poultry, domestic animals and the like, the compositions can be applied as formulations (for example powders, emulsions, flowables) comprising the active ingredients in an amount of 1 to 80% by weight, either directly or after 100- to 10 000-fold dilution, or they may be used as a chemical dip.

It has also been found that the inventive insecticidal compositions have a strong insecticidal action against insects which destroy industrial materials.

The following insects may be mentioned as examples and as preferred—but without a limitation:

beetles, such as *Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;*

Dermapterans, such as *Sirex juvencus, Urocerus gigas, Urocerus gigas taignus, Urocenis augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes fonnosanus;*

Bristletails, such as *Lepisma saccarina.*

Industrial materials in the present connection are to be understood as meaning non-living materials, such as, preferably, plastics, adhesives, sizes, papers and cards, leather, wood, processed wood products and coating compositions.

The ready-to-use compositions can also comprise other insecticides, if appropriate, and also one or more fungicides, if appropriate.

With respect to possible additional partners for mixing, reference is made to the insecticides and fungicides mentioned above.

At the same time, the inventive compositions can be employed for protection of objects which come into contact with saltwater or brackish water, especially hulls, screens, nets, buildings, moorings and signaling systems, against fouling.

In addition, the inventive compositions can be used alone or in combinations with other active ingredients as antifouling compositions.

The compositions are also suitable for controlling animal pests in the household, in hygiene and in the protection of stored products, in particular insects, arachnids and mites, which are found in enclosed spaces such as, for example, dwellings, factory halls, offices, vehicle cabins and the like. They can be employed alone or in combination with other active ingredients and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodoros moubat, Rhipicephalus sanguineus, Trombicula alfreddugesi, Neutrombicula autumnalis, Dennatophagoides pteronissimus, Dermatophagoides forinae.*

From the order of the Araneae, for example, *Avculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active ingredients, such as phosphoric acid esters, carbamates, pyrethroids, neonicotinoids, growth regulators or active ingredients from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

When the inventive compositions comprise at least one active fungicidal ingredient, they possess very good fungicidal properties and can be used for control of phytopathogenic fungi, such as *Plasmo-diophoromycetes, Oomycetes, Chytridiomycetes, Zygomycetes, Ascomycetes, Basidiomycetes, Deuteromycetes* etc.

Illustrative but non-limiting examples of pathogens which cause fungal diseases covered by the generic names listed above are as follows:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondita* or *Puccinia triticina*; *Uromyces* species, for example *Uromyces appendiculatus*;

diseases caused by pathogens from the group of the Oomycetes, for example *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Altemaria* species, for example *Altemaria solani*; *Cercospora* species, for example *Cercospora beticola*; *Cladiosporium* species, for example *Cladiosporium cucumerinum*; *Cochliobolus* species, for example *Cochliobolus sativus* (conidia form: Drechslera, syn: Helminthosporium); *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Mycosphaerella* species, for example *Mycosphaerella graminicola*; *Phaeosphaeria* species, for example *Phaeosphaeria nodorum*; *Pyrenophora* species, for example *Pyrenophora teres*; *Ramularia* species, for example *Ramularia collo-cygni*; *Rhynchosporium* species, for example *Rhynchosporium secalis*; *Septoria* species, for example *Septoria apii*; *Typhula* species, for example *Typhula incarnata*; *Venturia* species, for example *Venturia inaequalis*;

root and stem diseases caused, for example, by *Corticium* species, for example *Corticium gramineamm*; *Fusarium* species, for example *Fusarium oxysporum*; *Gaeumannomyces* species, for example *Gaeumannomyces graminis*; *Rhizoctonia* species, such as, for example *Rhizoctonia solani*; *Tapesia* species, for example *Tapesia actifonnis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium* spp.; *Claviceps* species, for example *Claviceps purpurea*; *Fusarium* species, for example *Fusarium culmorum*; *Gibberella* species, for example *Gibberella zeae*; *Monographella* species, for example *Monographella nivalis*;

diseases caused by smut fungi, for example *Sphacelotheca* species, for example *Sphacelotheca reiliana*; *Tilletia* species, for example *Tilletia caries*; *Urocystis* species, for example *Urocystis occulta*; *Ustilago* species, for example *Ustilago nuda*;

fruit rot caused, for example, by *Aspergillus* species, for example *Aspergillus flavus*; *Botrytis* species, for example *Botrytis cinerea*; *Penicillium* species, for example *Penicillium expansum*; *Sclerotinia* species, for example *Sclerotinia sclerotiorum*; *Verticilium* species, for example *Verticilium alboatrum*;

seed- and soil-borne rot and wilt diseases, and also diseases of seedlings, caused, for example, by *Fusarium* species, for example *Fusarium culmorum*; *Phytophthora* species, for example *Phytophthora cactorum*; *Pythium* species, for example *Pythium ultimum*; *Rhizoctonia* species, for example *Rhizoctonia solani*; *Sclerotium* species, for example *Sclerotium rolfsii*;

cancerous diseases, galls and witch's broom caused, for example, by *Nectria* species, for example *Nectria galligena*;

wilt diseases caused, for example, by *Monilinia* species, for example *Monilinia laxa*;

deformations of leaves, flowers and fruits caused, for example, by *Taphrina* species, for example *Taphrina deformans*;

degenerative diseases of woody plants caused, for example, by *Esca* species, for example *Phaeomoniella chlamydospora*;

diseases of flowers and seeds caused, for example, by *Botrytis* species, for example *Botrytis cinerea*;

diseases of plant tubers caused, for example, by *Rhizoctonia* species, for example *Rhizoctonia solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Preference is given to controlling the following diseases of soybeans:

Fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive compositions which comprise at least one active herbicidal ingredient (=herbicidal compositions) have an outstanding herbicidal efficacy against a broad spectrum of economically important mono- and dicotyledonous harmful plants. It is unimportant whether the substances are applied before sowing, pre-emergence or post-emergence.

Specific examples of some representatives of the monocotyledonous and dicotyledonous weed flora which can be controlled by the inventive compounds are as follows, though the enumeration is not intended to impose a restriction to particular species.

Among the monocotyledonous grass species, the compounds act efficiently, for example, both against self-sown cereals, such as wheat, barley, rye and triticale, and, for example, against *Apera spica venti, Avena* spp., *Alopecurus* spp., *Brachiaria* spp., *Digitaria* spp., *Lolium* spp., *Echinochloa* spp., *Panicum* spp., *Phalaris* spp., *Poa* spp., *Setaria* spp. and also *Bromus* spp., such as *Bromus catharticus, Bromus secalinus, Bromus erectus, Bromus tectorum* and *Bromus japonicus*, and *Cyperus* species from the annual group and, among the perennial species, *Agropyron, Cynodon, Imperata* and *Sorghum*, and also perennial *Cyperus* species.

In the case of the dicotyledonous weed species, the spectrum of action extends to species such as, for example, *Abutilon* spp., *Amaranthus* spp., *Chenopodium* spp., *Chrysanthemum* spp., *Galium* spp., *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., *Papaver rhoeas* spp., *Centaurea* spp. among the annual species, and also *Convolvulus, Cirsium, Rumex* and *Artemisia* spp. among the perennial weeds.

If the inventive herbicidal compositions are applied to the soil surface before germination, either the weed seedlings are prevented completely from emerging or the weeds grow until they have reached the cotyledon stage, but then stop growing, and eventually, after three to four weeks have elapsed, die completely.

If the active ingredients are applied post-emergence to the green parts of the plants, there is likewise a severe stoppage of growth very rapidly after the treatment, and the weed plants remain at the growth stage of the time of application, or they die completely after a certain time, such that competition by the weeds, which is harmful to the crop plants, is thus eliminated very early and in a lasting manner.

The inventive herbicidal compositions are notable for a rapidly commencing and long-lasting herbicidal action. The rainfastness of the active ingredients in the inventive combinations is generally favorable. The inventive combination of active ingredients allows the necessary application rate of the active ingredients to be reduced considerably.

The inventive herbicidal compositions have an outstanding herbicidal efficacy against a broad spectrum of economically important mono- and dicotyledonous harmful plants, including species which are resistant to active herbicidal ingredients such as glyphosate, glufosinate, atrazine or imidazolinone herbicides.

Even though the inventive herbicidal compositions have an outstanding herbicidal activity toward mono- and dicotyledonous harmful plants, the crop plants are damaged only to a minor degree, if at all.

Furthermore, some inventive compositions have outstanding growth-regulating properties with respect to the crop plants. They intervene in the plant's own metabolism with a regulatory effect, and can thus be used to control plant constituents and to facilitate harvesting, for example by triggering desiccation and stunted growth. In addition, they are also suitable for general control and inhibition of unwanted vegetative growth without killing the plants. Inhibition of vegetative growth is very important for many mono- and dicotyledonous crops, since this can reduce or completely prevent harvesting losses caused by lodging.

Owing to their herbicidal and plant growth-regulating properties, the inventive compositions can be used to control harmful plants in genetically modified crop plants, or those obtained by mutation and selection. These crop plants are generally notable for particularly advantageous properties, such as resistances to herbicidal compositions or resistances to plant diseases or pathogens of plant diseases, such as particular insects, or microorganisms such as fungi, bacteria or viruses. Other particular properties relate, for example, to the harvested material with regard to quantity, quality, storability, composition and specific constituents. Known examples include transgenic plants with increased starch content or altered starch quality, or those with a different fatty acid composition of the harvested material.

Conventional ways of generating novel plants which have modified properties compared to existing plants consist, for example, in traditional breeding methods and the generation of mutants (see, for example, U.S. Pat. No. 5,162,602; U.S. Pat. No. 4,761,373; U.S. Pat. No. 4,443,971). Alternatively, it is possible to obtain novel plants with altered properties with the aid of recombinant methods (see, for example, EP-A-0221044, EP-A-0131624). For example, there have been descriptions in several cases of:

genetic modifications of crop plants for the purpose of modifying the starch synthesized in the plants (for example WO 92/11376, WO 92/14827, WO 91/19806),
  transgenic crop plants which are resistant to other herbicides, for example to sulfonylureas (EP-A-0 257 993, U.S. Pat. No. 5,013,659), to glyphosate (Round-up Ready© cultivars), to glufosinate (LibertyLink© cultivars) or to imidazolinones,
  transgenic oilseed rape plants, for example imidazolinone-resistant oilseed rape cultivars, Roundup Ready© oilseed rape (RR-oilseed rape) or LibertyLink© oilseed rape (LL-oilseed rape), transgenic crop plants having the ability to produce *Bacillus thuringiensis* toxins (Bt toxins) which make the plants resistant to particular pests (EP-A-0142924, EP-A-0193259), transgenic crop plants having a modified fatty acid composition (WO 91/13972).

A large number of molecular biology techniques with which novel transgenic plants with modified properties can be generated are known in principle; see, for example, Sambrook et al., 1989, Molecular Cloning, A Laboratory Manual, 2nd edition, Cold Spring Harbor Laboratory Press, Cold Spring Harbor, N.Y.; or Winnacker "Gene and Klone" ["Genes and Clones"], VCH Weinheim 2nd edition 1996 or Christou, "Trends in Plant Science" 1 (1996) 423-431.

For such recombinant manipulations, nucleic acid molecules which allow mutagenesis or sequence alteration by recombination of DNA sequences can be introduced into plasmids. For example, the abovementioned standard methods allow base exchanges to be conducted, subsequences to be removed, or natural or synthetic sequences to be added. To connect the DNA fragments to each other, adapters or linkers may be added to the fragments.

For example, the production of plant cells with a reduced activity of a gene product can be achieved by expressing at least one corresponding antisense RNA, or a sense RNA to achieve a cosuppression effect, or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized can be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give rise to entire plants. In principle, the transgenic plants may be plants of any desired plant species, i.e. not only monocotyledonous but also dicotyledonous plants. Thus, it is possible to obtain transgenic plants whose properties are altered by overexpression, suppression or inhibition of homologous (=natural) genes or gene sequences, or expression of heterologous (=foreign) genes or gene sequences.

The present invention further also provides a method for controlling unwanted plant growth (for example harmful plants), preferably in crop plants such as cereals (e.g. wheat, barley, rye, oats, crossbreeds thereof, such as triticale, rice, corn, millet), sugar beet, sugar cane, oilseed rape, cotton and soya bean, more preferably in monocotyledonous crops such as cereals, for example wheat, barley, rye, oats, crossbreeds thereof, such as triticale, rice, corn and millet, or in dicotyledonous crops, wherein one or more herbicides of type (A) and one or more herbicides of type (B) are applied jointly or separately, for example pre-emergence, post-emergence or pre- and post-emergence, to the plants, for example harmful plants, plant parts, plant seeds or the area on which the plants grow, for example the area under cultivation.

The plant crops may also have been genetically modified or obtained by mutation selection.

The inventive herbicidal compositions may also be used nonselectively for control of unwanted vegetation, for example in plantation crops, on roadsides, squares, industrial sites or railway tracks.

The preparation and use examples which follow illustrate the invention without restricting it in any way.

PREPARATION EXAMPLES

To prepare a suspension concentrate, all liquid components are first mixed with one another. In the next step, the solids are added and stirred until a homogeneous suspension is obtained. The homogeneous suspension is subjected first to a coarse and then to a fine grinding operation, so as to obtain a suspension in which 90% of the solid particles have a particle size below 5 μm. Subsequently added while stirring at room temperature to the thickener preliminary solution and water. A homogeneous suspension concentrate is obtained.

The examples which follow illustrate the invention without limiting it in any way. All figures are in % by weight.

TABLE 1

Compositions of inventive formulations (% by weight)

| | Example | | |
|---|---|---|---|
| | 1 | 2 | 3 |
| imidacloprid | | | 10.6 |
| spirotetramat | 9.2 | | 10.6 |
| thiacloprid | | 21.7 | |
| Crovol ® CR 70 G | 15 | 20 | 15 |
| glycerol | 10 | 10 | |
| Synergen IB ® 775 | | | 5 |
| Soprophor TS ® 29 | 4 | | |
| Atlox ® 4913 | | 3 | 3 |
| Soprophor TS ® 54 | | 1 | 3 |
| Kelco ® VIS-DG | 0.12 | 0.03 | 0.15 |
| Preventol ® D7 | 0.08 | 0.08 | 0.08 |
| Proxel ® GXL | 0.12 | 0.12 | 0.12 |
| Silfoam ® SRE | 0.1 | 0.1 | 0.1 |
| citric acid | 0.1 | | 0.1 |
| water | 61.28 | 43.97 | 52.25 |

Comparative Examples

To prepare a comparative example, all liquid components are first mixed with one another. In the next step, the solids are added and stirred until a homogeneous suspension is obtained. The homogeneous suspension is subjected first to a coarse and then to a fine grinding operation, so as to obtain a suspension in which 90% of the solid particles have a particle size below 5 μm. Subsequently, Kelzan® S and water are added while stirring at room temperature. A homogeneous suspension concentrate is obtained.

TABLE 2

Compositions of comparative formulations (% by weight)

| | Comparative example | | |
|---|---|---|---|
| | 1 | 2 | 3 |
| imidacloprid | | | 10.6 |
| spirotetramat | 9.2 | | 10.6 |
| thiacloprid | | 21.7 | |
| Crovol ® CR 70 G | 15 | 20 | 15 |
| glycerol, 99.5% | 10 | 10 | |
| Synergen ® IB 775 | | | 5 |
| Soprophor TS ® 29 | 4 | | |
| Atlox ® 4913 | | 3 | 3 |
| Soprophor TS ® 54 | | 1 | 3 |
| Kelzan S ® | 0.1 | 0.08 | 0.1 |
| Preventol ® D7 | 0.08 | 0.08 | 0.08 |
| Proxel ® GXL | 0.12 | 0.12 | 0.12 |
| Silfoam ® SRE | 0.1 | 0.1 | 0.1 |
| citric acid | 0.1 | | 0.1 |
| water | 61.3 | 43.92 | 52.3 |

Storage Stability of the Inventive Formulations

To determine storage stability, 100 ml of formulation were stirred under varying temperature conditions (VT) or at 54° C. for two or eight weeks. The varying temperature conditions are 48 hours at 30° C., lowering the temperature within 22.5 hours at 2° C./hour to −15° C., 75 hours at −15° C., in 22, increasing the temperature over the course of 5 hours at 2° C./hour to 30° C. After the storage, the sample is brought to room temperature and the degrees of phase separation, dispersibility and viscosity are determined. For comparison, the starting values are also listed. In addition to the viscosity, the cup efflux time (measured to DIN 53211) is another starting value given. The cup efflux time (CET) is a number which simulates the ability of the product to be poured out of a bottle. Values between 45 and 70 sec are optimal here.

The extent of phase separation, also referred to as syneresis (Syn), is expressed in % (5% means 5% clear phase to 95% suspension). Dispersibility (DISP) is determined by the CIPAC MT 180 method after 24 hours, and dynamic viscosity (Visc) is measured at 7.5 s$^{-1}$ on a Haake RheoStress RS 150.

After the desired time, the kill in % is determined. 100% means that all aphids have been killed; 0% means that no aphids have been killed.

In this test, for example, the following formulations exhibit superior efficacy to the prior art:

TABLE 4

Myzus persicae test

| Formulation | Concentration in g/ha | Kill in % after 3 days |
|---|---|---|
| Example 1 | 150 | 25 |
| Comparative example 1 | 150 | 0 |
| Example 2 | 48 | 95 |
| Comparative example 2 | 48 | 15 |

Determination of the Plant Compatibility of Different Spirotetramat/Adjuvant Combinations Plant compatibility of spray liquors prepared with the formulations from examples 1, 2 and 3 (0.2 g of active ingredient/l) was determined in tap water on bell pepper leaves (*Capsicum annum* cv. Pusta Gold).

TABLE 5

Plant compatibility of spirotetramat

| BYI8330 (0.2 g/l) + additive (0.5 g/l) | Necrosis on bell pepper leaves* after 1 day | Necrosis on bell pepper leaves* after 6 days |
|---|---|---|
| Inventive | | |
| Example 1 | 0 | 0 |
| Example 2 | 0 | 0 |
| Example 3 | 0 | 0 |
| Comparative | | |
| Genapol C100 | 1 | 3 |

*0 = no necrosis; 1 = slight spotty necrosis on leaf area wetted by the droplet, 2 = ring-shaped necrosis, 3 = maximum necrosis over whole area 2×10 μl droplets per additive were applied to each leaf, one to each half of the leaf, as defined by the middle veins. Several

TABLE 3

Storage stability of the inventive formulations

| | Starting value | | | 2 weeks at 54° C. | | | 4 weeks of VT | | | 8 weeks at 54° C. | | | 8 weeks of VT | | |
|---|---|---|---|---|---|---|---|---|---|---|---|---|---|---|---|
| | CET in sec | Disp in ml | Visc/ mPas | Syn in % | Disp in ml | Visc/ mPas | Syn in % | Disp in ml | Visc/ mPas | Syn in % | Disp in ml | Visc/ mPas | Syn in % | Disp in ml | Visc/ mPas |
| Example 1 | 62 | 0.1 | 299 | 0 | 0.1 | 251 | 0 | 0.1 | 290 | 2 | 0.2 | 287 | 0 | 0.2 | 294 |
| Example 2 | 68 | 0.1 | 324 | 7 | 0.4 | 227 | 0 | 0.2 | 313 | 12 | 0.3 | 276 | 0 | 0.2 | 307 |
| Example 3 | 58 | 0.1 | 379 | 3 | 0.3 | 265 | 0 | 0.2 | 348 | 12 | 0.2 | 261 | 0 | 0.1 | 342 |
| Comparative example 1 | 51 | 0.3 | 354 | 31 | 0.5 | 171 | 2 | 0.2 | 343 | 46 | 0.3 | 165 | 2 | 0.2 | 180 |
| Comparative example 2 | 70 | 0.1 | 427 | | | | | | | 44 | 0.2 | 439 | 1 | 0.1 | 393 |
| Comparative example 3 | 56 | 0.3 | 364 | | | | | | | 30 | 0.4 | 282 | 10 | 0.1 | 368 |

Determination of Biological Efficacy:

Test Description: Myzus Persicae Test

To prepare an appropriate preparation solution, 1 part by weight of formulated material is mixed with water to the desired concentration.

Cabbage leaves (*Brassica oleracea*) severely infested by the green peach aphid (*Myzus persicae*) are treated with the preparation solution in the desired concentration.

additives were applied to one leaf (top side), and several leaves from the same plant were used. As an internal standard for typical reaction of the leaf, Genapol C-100 (0.5 g/l) was also applied in the foremost third of the leaf, which causes ring-shaped necrosis. During application and drying, the relative air humidity was 30-40% and the temperature was ~21° C.

The evaluation was effected visually using an evaluation template. In addition, pictures were taken with a digital camera. In order to rule out the risk of spray residues being identified as damage, all application sites have been stripped with cellulose acetate, and a further assessment was made after removal of the spray residue.

The invention claimed is:

1. A water-dispersed agrochemical composition, comprising
   (a) 1 to 60% by weight of at least one active agrochemical ingredient, wherein the at least one active agrochemical ingredient is selected from the group consisting of spirotetramat, tebuconazole, prothioconazole, tembotrione, thiacloprid, fluopicolide and imidacloprid, and wherein the at least one active agrochemical ingredient is a solid at room temperature;
   (b) 1 to 50% by weight of at least one penetrant, wherein the at least one penetrant is obtained by ethoxylating rapeseed oil, the degree of ethoxylation being between 50% by weight and 80% by weight;
   (c) 0.005 to 1% by weight of a at least one thickener, wherein the at least one thickener is an anionic polysaccharide which contains, as the repetitive base unit in the main chain, four sugar molecules containing glucose, glucuronic acid, glucose, and rhamnose;
   (d) 1 to 20% by weight of at least one nonionic or at least one anionic surfactant; and
   (e) 0.1 to 25% by weight of one or more additives selected from the group consisting of foam inhibitors, preservatives, antioxidants, spreaders, and dyes;
wherein the composition is the form of a suspension concentrate.

2. A method for controlling animal pests, phytopathogenic fungi, or unwanted plant growth, comprising applying an effective amount of the composition of claim 1 to unwanted plants, animal pests, phytopathogenic fungi, the surroundings of plants, the habitat of plants, or the storage space of plants.

3. A method for controlling animal pests, wherein the composition of claim 1 is applied diluted or undiluted to animal pests or the habitat of an animal pest.

4. A method for controlling phytopathogenic fungi or unwanted plant growth, wherein the composition of claim 1 is applied diluted or undiluted to plants, plant parts, plant seeds, or the area on which the plants grow.

5. A water-dispersed agrochemical composition, comprising:
   (a) 1 to 60% by weight of at least one active agrochemical ingredient, wherein the at least one active agrochemical ingredient is selected from the group consisting of spirotetramat, tebuconazole, tembotrione, thiacloprid, fluopicolide and imidacloprid, and wherein the at least one active agrochemical ingredient is a solid at room temperature;
   (b) 1 to 20% by weight of at least one penetrant, wherein the at least one penetrant is obtained by ethoxylating rapeseed oil, the degree of ethoxylation being between 60% by weight and 80% by weight;
   (c) 0.005 to 1% by weight of at least one thickener, wherein the at least one thickener is an anionic polysaccharide which contains, as the repetitive base unit in the main chain, four sugar molecules containing glucose, glucuronic acid, glucose, and rhamnose;
   (d) 1 to 20% by weight of at least one nonionic or at least one anionic surfactant;
   (e) 0.1 to 25% by weight of one or more additives selected from the group consisting of foam inhibitors, preservatives, antioxidants, spreaders, and dyes; and
   (f) water;
wherein the composition is in the form of a suspension concentrate.

* * * * *